United States Patent [19]
Tanner et al.

[11] Patent Number: 6,106,675
[45] Date of Patent: Aug. 22, 2000

[54] METHOD OF MICROWAVE BOND CLEAVAGE OF A HYDROCARBON COMPOUND IN A LIQUID PHASE

[75] Inventors: Dennis D. Tanner; Qizhu Ding; Pramod Kandanarachchi, all of Edmonton, Canada; James A. Franz, Kennewick, Wash.

[73] Assignees: Battelle Memorial Institute, Richland, Wash.; Governors of the University of Alberta, Edmonton, Canada

[21] Appl. No.: 09/122,530

[22] Filed: Jul. 24, 1998

[51] Int. Cl.[7] .................................................... C07F 01/00
[52] U.S. Cl. ............................... 204/157.6; 204/157.15; 204/157.3; 204/157.43; 204/157.46; 204/157.47; 204/157.52
[58] Field of Search ........................... 204/157.6, 157.43, 204/157.3, 157.46, 157.47, 157.52, 157.15

[56] References Cited

U.S. PATENT DOCUMENTS

| | | | |
|---|---|---|---|
| 4,279,722 | 7/1981 | Kirkbride | 204/162 |
| 4,306,101 | 12/1981 | Slaugh et al. | 568/899 |
| 4,574,038 | 3/1986 | Wan | 204/162 |
| 4,975,164 | 12/1990 | Ravella et al. | 204/156 |
| 5,025,912 | 6/1991 | Murphy | 204/157.15 |
| 5,131,993 | 7/1992 | Suib et al. | 204/168 |
| 5,181,998 | 1/1993 | Murphy et al. | 204/157.15 |
| 5,266,175 | 11/1993 | Murphy | 204/157.43 |
| 5,269,892 | 12/1993 | Cha | 204/157.3 |
| 5,277,773 | 1/1994 | Murphy | 204/168 |
| 5,328,577 | 7/1994 | Murphy | 204/168 |
| 5,472,581 | 12/1995 | Wan | 204/157.6 |

FOREIGN PATENT DOCUMENTS

| | | | |
|---|---|---|---|
| 0435591A2 | 7/1991 | European Pat. Off. | C07C 11/24 |
| 91/04622 | 6/1991 | WIPO | G01B 13/00 |

OTHER PUBLICATIONS

Dimerization of Methane Through Microwave Plasmas, J Huang, SL Suib, American Chemical Society, 1993.

A Direct, Continuous, Low–Power Catalytic Conversion of Methane To Higher Hydrocarbons Via Microwave Plasmas, SL Suib, RP Zerger, Journal of Catalysis 139, 383–381, 1993.

Primary Examiner—Kathryn Gorgos
Assistant Examiner—Jonathan Brown
Attorney, Agent, or Firm—Paul W. Zimmerman

[57] ABSTRACT

The method of the present invention is a microwave bond cleavage of a first hydrocarbon compound, the first hydrocarbon compound in a liquid phase and substantially non-aqueous, to a second compound having a shorter carbon chain than the first hydrocarbon compound. The method has the steps of exposing a combination of the first hydrocarbon compound with a supported catalyst having a carrier of a non-metallic amorphous solid with at least one catalytic metal dispersed therein to microwave energy thereby converting the first hydrocarbon compound into the second hydrocarbon compound, and recovering the second hydrocarbon compound. Advantages of the present invention include use of a low cost supported catalyst at ambient temperature and pressure.

24 Claims, 2 Drawing Sheets

Squalane

METHOD OF MICROWAVE BOND CLEAVAGE OF A HYDROCARBON COMPOUND IN A LIQUID PHASE

FIELD OF THE INVENTION

The present invention is a method of microwave bond cleavage of a hydrocarbon compound in a liquid phase. In other words, microwave conversion of long chain hydrocarbons to shorter chain unsaturated hydrocarbons and molecular hydrogen or dihydrogen.

BACKGROUND OF THE INVENTION

Bond cleavage for converting long chain hydrocarbons to short chain unsaturated hydrocarbons is important in the commodity chemicals industry. Methods for the direct cleavage of alkane carbon—carbon bonds in organic molecules are used for both commodity chemicals and fuels and for selective synthesis of specialty chemicals. Useful chemicals include α-olefins, lower molecular weight hydrocarbons with olefin sites, isomers of saturated and partially unsaturated hydrocarbons, ring contracted cyclic hydrocarbon, olefinic monomers such as methyl acrylate, ethylene, propylene, butene, and combinations thereof. Present conversion methods, including multi-step synthetic methods, require heat and pressure.

There has been a long felt need in the art of thermal liquid phase hydrocarbon conversions for methods capable of operating at reduced temperature and pressure.

SUMMARY OF THE INVENTION

The method of the present invention is a microwave bond cleavage of a first hydrocarbon compound, the first hydrocarbon compound in a liquid phase and substantially non-aqueous, to a second compound having a shorter carbon chain than the first hydrocarbon compound. The method has the steps of exposing a combination of the first hydrocarbon compound with a supported catalyst having a carrier or support of a non-metallic amorphous solid with at least one catalytic metal dispersed s therein to microwave energy thereby converting the first hydrocarbon compound into the second hydrocarbon compound, and recovering the second hydrocarbon compound.

Advantages of the present invention include use of a low cost supported catalyst at ambient temperature and pressure.

Accordingly, it is an object of the present invention to provide a method of catalyzed microwave conversion of a liquid hydrocarbon to a shorter chain unsaturated hydrocarbon and molecular hydrogen.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
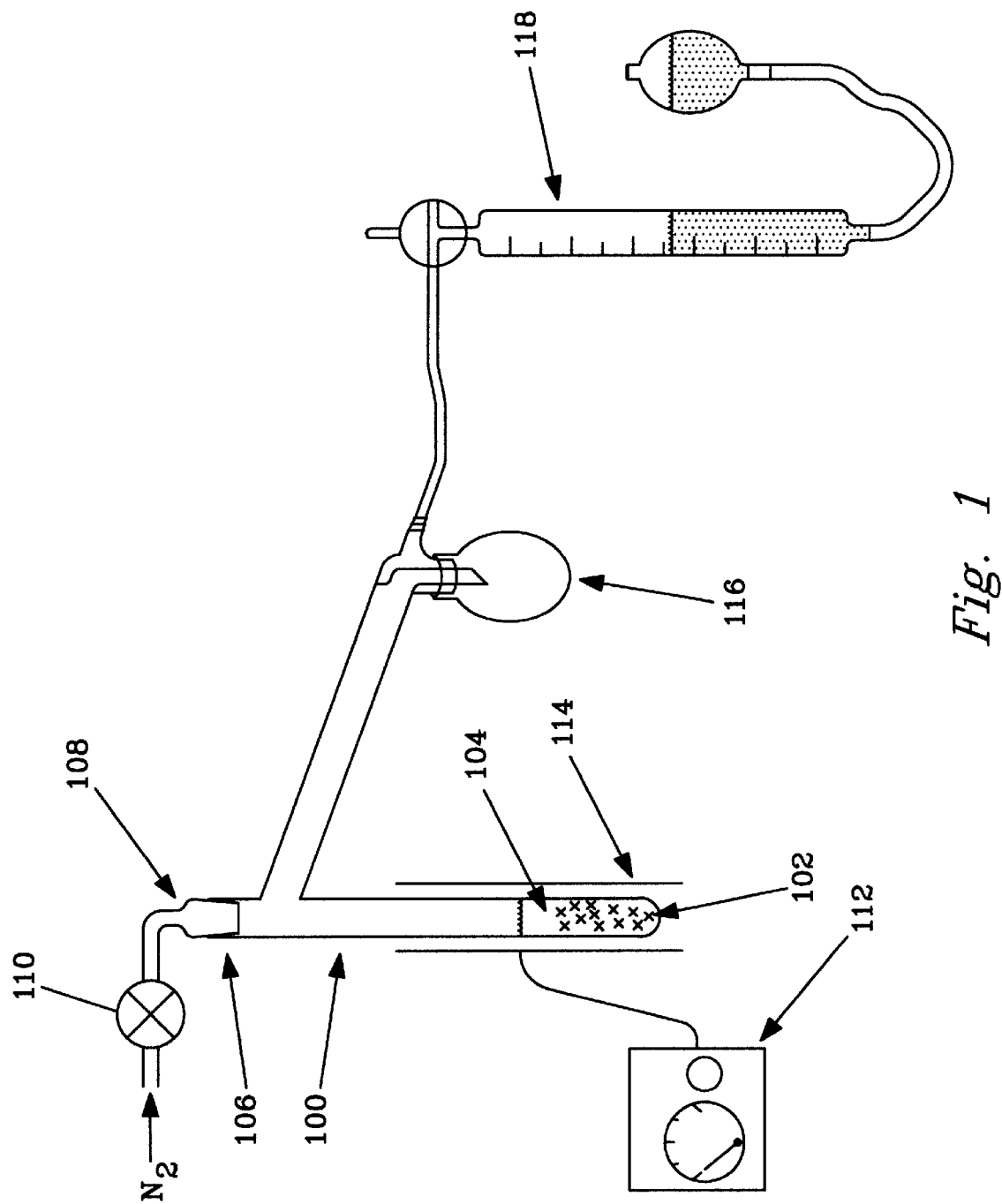
FIG. 1 is a schematic of an apparatus for conversion of polymer melts and liquid hydrocarbons to liquid and gaseous products.

The method of the present invention is directed to microwave bond cleavage of a first hydrocarbon compound, the first hydrocarbon compound in a liquid phase and substantially non-aqueous resulting in a product of a second compound having a shorter carbon chain than the first hydrocarbon compound. The method has the steps of (a) exposing a combination of the first hydrocarbon compound with a supported catalyst having a support of a non-metallic amorphous solid with at least one catalytic metal dispersed therein to microwave energy thereby converting the first hydrocarbon compound into the second hydrocarbon compound.; and (b) recovering the second hydrocarbon compound. The order of sub-steps in step (a) is not critical to the present invention. It is preferred that the first hydrocarbon compound be combined with the supported catalyst in advance of microwave exposure. However, the catalyst and microwave energy may be present in advance of introducing the first hydrocarbon compound.

While the oxidative bond cleavage (resulting in a product with a reduced ratio of hydrogen to carbon), or non-oxidative bond cleavage (resulting in a product with the same hydrogen to carbon ratio) is selective and robust, excessive water may retard the reaction rate. Accordingly, it is preferred that no molecular water (liquid or gas), or an amount of molecular water that is ineffective to retard the reaction rate be present in either the supported catalyst or the first hydrocarbon compound.

The first hydrocarbon compound is a liquid at room temperature and has at least five (5) carbon atoms in a chain. The first hydrocarbon compound includes but is not limited to linear chain hydrocarbon, branched hydrocarbon, cyclic hydrocarbon, and combinations thereof. Linear chain hydrocarbon includes, for example polyethylene and co-polymers. Branched hydrocarbon includes, for example squalane. Cyclic hydrocarbon includes, for example benzene, cyclododecane, cyclodecane, cyclooctane, and cyclohexane and combinations thereof. Any type of first hydrocarbon compound may be further derivatized by replacing a hydrogen atom in the compound with a functional group, which may include hydroxyl (—OH), cyano (—CN), carboxylate (—CO$_2$H), or ester (—CO$_2$R, R=alkyl). Derivatized compounds include but are not limited to carboxylic acid, nitrile, alcohol, ester, and combinations thereof. It has been found that the functional groups of the derivatized compound are substantially unaffected by the bond cleavage of an alkyl carbon—carbon bond in the same molecule. Moreover, molecular hydrogen is a product of the terminal olefin formation. Substantially unaffected means that greater than 90% up to and including 100% of the derivatized compound is unaffected.

The bond cleavage produces olefins, especially α-olefins, from linear hydrocarbon compounds, underivatized or derivatized. A desirable reaction is bond cleavage of dimethyladipate producing methyl acrylate. Another desirable reaction is cleaving an aliphatic organic ester (such as methyl palmitate) to an ester with an olefin group on one end of the aliphatic chain with the ester group on the other end. Another desirable reaction is the conversion of aliphatic carboxylic acids such as hexadecanoic acids to carboxylic acids of varying carbon length substituted with a terminal olefin group. More generally, the present invention is useful for making polymer olefinic precursor, for example acrylate, directly from saturated alkyl carboxylate ester. Another reaction suitable to the present invention is the selective introduction of oxygen into an organic molecule resulting in a ketone or an alcohol; an example is the conversion of a cyclic alkane in the presence of small quantities of water as an oxygen source to a cyclic ketone or a cyclic alcohol. Oxidative bond cleavage of branched hydrocarbon compounds produces lower molecular weight hydrocarbon compounds with olefin sites. More specifically, squalane cleaves to a mixture of branched alkene structures. The reaction of squalane illustrates that both terminal and secondary olefins may result from the reactions of branched hydrocarbons. The bond cleavage of cyclic hydrocarbon compounds produces ring opening, loss of ethylene units, isomerization, ring contraction and combinations thereof.

Nearly quantitative selectivity for the production of molecular hydrogen and terminal olefins in the liquid products has been achieved if the starting alkane is a linear alkane, and the conversion is halted at less than approximately 60%. At that extent of reaction, the liquid products ($C_5$ and larger hydrocarbons) exhibit as high as 98% terminal mono-olefin and only 2% of di-terminal olefin and saturated analogues. At higher conversions, terminal mono-olefins are converted to di-terminal olefins, and mono-terminal olefins are further degraded to light gases, primarily ethylene and molecular hydrogen. When polymer melts, such as molten low density polyethylene copolymer are reacted, mono- and di-terminal olefins result. By allowing the liquid products to distill from the reaction zone, a polymer may be completely converted to volatile olefinic hydrocarbons and light gases.

Non-metallic amorphous solids include but are not limited to carbon, alumina, manganese dioxide, magnetite, nickel oxide, iron oxide, calcium aluminate, cobalt oxide, chromium nitride, iron sulfide, copper sulfide.

Catalytic metal includes but is not limited to chromium (Cr), copper (Cu), iron (Fe), nickel (Ni), lead (Pb), zinc (Zn), boron (B), barium (Ba), magnesium (Mg), strontium (Sr), titanium (Ti), vanadium (V), phosphorus (P), manganese (Mn), molybdenum (Mo), silicon (Si), silver (Ag), aluminum (Al), cadmium (Cd), cobalt (Co) and combinations thereof. Unreactive elements are calcium (Ca), potassium (K), sodium (Na) and combinations thereof. The presence of unreactive elements is not harmful to the conversion of the gaseous hydrocarbon.

The amount of microwave energy is controlled to avoid excessive heating. Control may be either by controlling the amount of microwave energy supplied, by heat removal or both. It is preferred that the microwave energy per mass of catalyst be less than 1000 W/g, more preferably about 50 W/g.

The physical or geometric form of the supported catalyst has been investigated for char. It is preferred that the char be in pieces of a size in excess of powder form. In other words, particle sizes are preferably greater than material that would pass a 100 mesh screen. Chunks or pieces of 1/16 inch to 1/4 inch mesh or larger are preferred. Rods of at least 1/16 inch diameter and up to about 3 inches in length perform equally well.

In a preferred embodiment, a ratio of at least one catalytic metal to the support plus at least one catalytic metal is less than 0.5 mg/10 mg support.

In a most preferred embodiment, the support and catalytic metal occur together wherein the non-metallic amorphous solid is carbon, for example a char. The char may be wood char, charcoal, and combinations thereof. Wood char may be produced by exposing wood in a non-oxidative atmosphere to an elevated temperature. For example, slivers of white pine placed in a nitrogen atmosphere and heated to a temperature from about 700° C. to about 900° C. for a time of from about 10 min to about 45 min produces an acceptable supported catalyst. Charcoal may be obtained from any source, but is most commonly obtained from charcoal, petroleum charcoal and combinations thereof. Table 1 shows an analysis of non-carbon elements present in the three chars.

TABLE 1

Analysis of Chars mg Element/10 mg Char[a]

| Element | White Pine Char | Wood Charcoal | Petroleum Charcoal |
|---------|-----------------|---------------|--------------------|
| Al | NA | 0.00775 | 0.0078 |
| Cd | NA | 0 | 0 |
| Co | NA | 0.0003 | 0.0001 |
| Cr | 0.00035 | 0.00195 | 0 |
| Cu | 0.00115 | 0.00145 | 0.001 |
| Fe | 0.00155 | 0.00035 | 0.00505 |
| Ni | 0.00585 | 0.0059 | 0.00015 |
| Pb | 0.00035 | 0 | 0 |
| Zn | 0.001 | 0.0061 | 0.0267 |
| B | 0.0016 | 0 | 0 |
| Ba | 0.00095 | 0.0264 | 0.00025 |
| Ca | 0.0464 | 26.9135 | 0.3823 |
| K | 0.4628 | 0.53715 | 0.08175 |
| Mg | 0.02145 | 0.0836 | 0.0345 |
| Sr | 0.00095 | 0.0934 | 0.00105 |
| Ti | 0 | 0 | 0 |
| V | 0.00005 | 0.00055 | 0.0001 |
| Na | 0.04765 | 0.0151 | 0.4673 |
| P | 0.0559 | 0.1431 | 0 |
| Mn | 0.0004 | 0.13575 | 0.0002 |
| Mo | 0.00075 | 0.0002 | 0.0002 |
| Si | 0 | 0 | 0 |
| Ag | 0.0007 | 0.00085 | 0 |

[a]10 mg of char was digested in 30 mL of Concentrated $HNO_3$. The $HNO_3$ Solution was evaporated to white powder. The white powder was dissolved in 50 mL water for ICP (Ion-Coupled Plasma) analysis.

EQUIPMENT USED IN EXAMPLES

Referring to FIG. 1, a reaction chamber 100 receives a supported catalyst having a carrier of a non-metallic amorphous solid with at least one catalytic metal dispersed therein 102 and liquid reactant sample 104. The top of the reactor 106 is closed with a closure 108 having an optional valve 110 thereon for sample addition and nitrogen flush prior to initiating the reaction. A microwave generator 112 (up to 50 w continuous power) connected to a microwave antenna or cavity 114 provides the microwave energy into the reaction vessel 100. As the reaction proceeds, liquid products are collected in a cold trap 116 and gaseous products are collected in a gas burette 118.

Example 1

An experiment was conducted to investigate the effect of the physical form of a char on the bond cleavage. The candidate compound was hexadecane. Three chars were used both in powdered form, or in larger pieces, specifically rods of at least 1/16 inch diameter and up to about 3 inches in length, and 6–14 mesh pieces. The char forms and conversion results are given in Table E1-1.

TABLE E1-1

Comparison of Char Form for Three Chars

| Char Type | % Conversion of Hexadecane | Reaction Time (min) |
|-----------|---------------------------|---------------------|
| Pine Char | | |
| Powdered | 7.5 | 50 |
| Rods | 22.0 | 50 |
| Petroleum Charcoal (Matheson) | | |
| Powdered | 9.3 | 75 |
| 6–14 mesh pieces | 14.6 | 75 |

TABLE E1-1-continued

Comparison of Char Form for Three Chars

| Char Type | % Conversion of Hexadecane | Reaction Time (min) |
|---|---|---|
| Decolorizing Charcoal (Caledon) Powdered | 0.0 | 75 |

Example 2

An experiment was conducted to demonstrate that derivative groups are substantially unaffected by the bond cleavage. Several derivatized compounds were tested.

Methyl Palmitate. A sample consisting of 0.1 g of pine charcoal and 1 g of the aliphatic organic ester, methyl palmitate, was exposed to a char and microwave energy for 1 hour according to the present invention. Products included gases (6.4% based on starting ester) and liquids (13.6% based on starting ester). A series of terminal olefins, $n-C_3H_7CH=CH_2$ through $n-C_{13}H_{27}CH=CH_2$ were produced along with a series of corresponding terminal olefins substituted with an ester group, $CH_3O_2C(CH_2)_nCH=CH_2$, n=4–12. The esters were produced in yields comparable to the simple terminal olefins, demonstrating that destruction of the ester group is an insignificant reaction pathway.

Octadecanol A sample of 0.05 g of pine char was combined with 1 g of substrate. Irradiation for 1 hour gave liquid products that contained a series of terminal olefins and a series of terminal olefins ($C_5$–$C_{17}$) with a terminal alcohol function.

Dimethyl Malonate 0.15 g of charcoal and 2.5 g substrate were irradiated for 2 hours. The compound was nearly inert, with only 4.0% gases formed and 1.2% of liquid products consisting of methanol and methyl acetate.

Diethyl Succinate 0.15 g of charcoal and 2.5 g substrate were irradiated for 2 hours. 10.3% conversion to gaseous products and 2.0% conversion to liquid products consisting of ethanol and ethyl acrylate occurred.

Dimethyl Adipate 0.1 g of charcoal and 1 g of substrate were irradiated. The products were methyl acrylate, methyl butenoate, and methyl pentenoate, formed in the ratio 20:5:1. These products composed 85% of the product mixture. Methyl proprionate, methyl butanoate, and methyl pentanoate were formed as 15% of the reaction mixture. Hydrogen was not quantitated in the reaction. These results suggest that dimethyl adipate was cleaved to form methylacrylate with 65% selectivity.

Hexadecanoic Acid. A 10-minute reaction of 0.075 g charcoal with 1 g of substrate gave gases (12% based on starting material) and liquids (23.7% based on starting material). The liquid fraction contained a series of terminal olefins ($C_5$–$C_{14}$) and a series of terminal olefins with a carboxylic acid function. The yields of carboxylic acids and terminal olefins were comparable. These results suggest that readily available fatty acids can be converted to olefinic carboxylic acids of varying carbon chain length by this method.

Example 3

An experiment was conducted to demonstrate oxidative bond cleavage of hexadecane for varied time exposure to microwaves. In a first test, an amount of 2 g of hexadecane was mixed with 0.5 g pine wood char, placed in a reaction tube and exposed to 25 W 2,540 MHz microwave radiation for 20 min. In a second test, 2.2 g of hexadecane and 0.3 g of pine char were irradiated for 100 minutes.

For both tests, gas chromatography, infrared gas chromatography and gas chromatography/mass spectrometry were used to identify product compounds. Results are shown in Tables E3-1 and E3-2.

TABLE E3-1

Products of Hexadecane for 20 minute Microwave Reaction

| Product Compound | GC Peak Area % |
|---|---|
| Gaseous Products | |
| $CH_4$ | 6.94 |
| $CH_2=CH_2$ | 79.43 |
| $CH_3CH_3$ | 4.58 |
| $CH_3CH=CH_2$ | 9.05 |
| Liquid Products | |
| $CH_2=CH_2$ | 0.545 |
| $CH_3CH=CH_2$ | 0.534 |
| $CH_3CH_2CH=CH_2$ | 0.0463 |
| $n-C_3H_7CH=CH_2$ | 0.0769 |
| $n-C_4H_9CH=CH_2$ | 0.1419 |
| $n-C_5H_{11}CH=CH_2$ | 0.1291 |
| $n-C_6H_{13}=CH_2$ | 0.3396 |
| $n-C_7H_{15}CH=CH_2$ | 0.6755 |
| $n-C_8H_{17}CH=CH_2$ | 0.7827 |
| $n-C_9H_{19}CH=CH_2$ | 0.7133 |
| $n-C_{10}H_{21}CH=CH_2$ | 0.6813 |
| $n-C_{11}H_{23}CH=CH_2$ | 0.6561 |
| $n-C_{12}H_{25}CH=CH_2$ | 0.5913 |
| $n-C_{13}H_{27}CH=CH_2$ | 0.3166 |
| $n-C_{16}H_{34}$ | 98.8658 |

The second experiment produced gases, 46.6%, and liquid products, 9.7%. The liquid products contained $C_5$ to $C_{15}$ terminal olefins (98% of liquids) About 2% of the liquid products were diterminal olefins and saturated hydrocarbon analogues of the terminal olefins. The main products are listed in Table E3-2.

TABLE E3-2

Products of Hexadecane for 100 minute Microwave

| Product | % Yield (Mole basis) |
|---|---|
| Liquid Products[a], 100-minute reaction | |
| $n-C_3H_7CH=CH_2$ | 0.59 |
| $n-C_4H_9CH=CH_2$ | 1.22 |
| $n-C_5H_{11}CH=CH_2$ | 1.24 |
| $n-C_6H_{13}=CH_2$ | 3.23 |
| $n-C_7H_{15}CH=CH_2$ | 14.7 |
| $n-C_8H_{17}CH=CH_2$ | 17.6 |
| $n-C_9H_{19}CH=CH_2$ | 14.8 |
| $n-C_{10}H_{21}CH=CH_2$ | 13.4 |
| $n-C_{11}H_{23}CH=CH_2$ | 13.2 |
| $n-C_{12}H_{25}CH=CH_2$ | 13.6 |
| $n-C_{13}H_{27}CH=CH_2$ | 6.27 |
| Gaseous Products[b] | |
| $H_2$ | 12.0 |
| $CH_4$ | 4.83 |
| $C_2H_4$ | 40.9 |
| $C_2H_6$ | 2.05 |
| $C_2H_2$ | 7.12 |
| $C_3H_6$ | 16.5 |
| $CH_3CH_2CH=CH_2$ | 8.16 |
| $CH_2=CHCH=CH_2$ | 5.79 |
| Others | 2.17 |

[a]Products normalized to 100%.
[b]Products normalized to 100%

Example 4

An experiment was conducted to demonstrate oxidative bond cleavage according to the present invention using polyethylene. An amount of 0.5 g of low density polyethylene was heated to melting (130° C.) then mixed with 0.2 g pine wood char. Microwave radiation of 50 W at 2,450 MHz was applied for a time of 30 min. The reaction produced gases (73%) and liquid products (27%). The products were allowed to distill from the reaction zone. The liquid fraction was dissolved in $CH_2Cl_2$. The liquid fraction contained $C_6$ to $C_{27}$ terminal olefins (70–80% of the products). Each olefin was accompanied by its corresponding diterminal olefin (3–8% of the mono-olefin yield) and the saturated hydrocarbon of the same carbon number (4–14% of the mono-olefin yield). The gaseous products contained $CH_4$ (4.5%), $C_2H_4$ (43%), $C_2H_6+C_2H_2$(6%), $CH_3CH=CH_2$ (26%), $CH_3CH_2CH=CH_2$ (8.4%) and 1,3-butadiene (12.5%). Hydrogen was not quantitated.

Example 5

An experiment was conducted to demonstrate oxidative bond cleavage of 1-phenyldodecane. Two chars were used as the catalyst. The first char was a wood based charcoal (CENCO, Central Scientific Company, USA) that was activated by heating to 700–800° C. under nitrogen atmosphere for 10 minutes (reactions 1–5). The second char was prepared by heating white pine splints to 700–800° C. under a nitrogen atmosphere for 10 minutes (reactions 6, 7).

An amount (1 g) of 1-phenyldodecane was mixed with the catalyst (0.05–0.1 g) and subjected to microwave radiation at 2,450 kHz for 10–60 minutes. The gaseous products were collected in a gas burette. The conversion to the gaseous products was quantitated by the weight loss of the reaction mixture during the reaction. The products were identified by their GC retention times, GC/IR and GC/MS and were compared to authentic materials.

Product Results are shown in Tables E5-1 through E5-3.

TABLE E5-1

The Gaseous Products From the Microwave Promoted Reactions of 1-Phenyldodecane With a Carbon Catalyst[a]

| Reaction | Reaction Time (min) | Conversion % | \multicolumn{8}{c}{Product Yield (%)[c]} |
|---|---|---|---|---|---|---|---|---|---|---|
| | | | $CH_4$ | $C_2H_4$ | $C_2H_6$ | $C_2H_2$ | $C_3H_6$ | 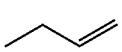 | 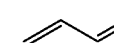 | 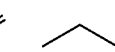 |
| 1 | 6  | 4.50 | 9.77 | 90.2 | Tr   | —    | —    | —    | —    | —    |
| 2 | 10 | 18.7 | 5.03 | 67.4 | 2.35 | 1.59 | 9.6  | 13.9 | —    | —    |
| 3 | 40 | 24.0 | 7.85 | 63.3 | 3.28 | 1.66 | 13.6 | 10.4 | —    | —    |
| 4 | 60 | 26.0 | 6.02 | 63.3 | 3.86 | 1.95 | 14.7 | 6.34 | 3.59 | 0.20 |
| 5 | 50 | 27.0 | 6.81 | 64.1 | 2.63 | 2.08 | 14.6 | 6.25 | 3.03 | 0.51 |
| 6 | 30 | 23.6 | 5.88 | 61.6 |      | 4.91 | 15.6 | 7.78 | 3.91 | 0.35 |
| 7 | 60 | 44.5 | 6.13 | 53.6 |      | 6.61 | 18.0 | 7.55 | 2.99 | 0.1  |

[a]Reactions 1–5 were carried out using 0.1 g of wood based charcoal. Reactions 6–7 were carried out using activated white pine splints, 0.5 and 0.05 g, respectively.
[b]Although hydrogen gas was formed it was not quantitated in this experiment.

TABLE E5-2

The products from the liquid fraction of the microwave promoted
reaction of 1-phenyldodecane with a wood charcoal catalyst.[a]

| Products[b] | | Product Yield (%), Reactions 1–4 | | | |
|---|---|---|---|---|---|
| A | 1-pentene | 0.2 | <0.1 | 0.28 | 0.42 |
| B | 1-hexene | 1.7 | 0.25 | 0.75 | 1.02 |
| C | benzene | 1.7 | 1.11 | 2.02 | 0.97 |
| D | 1-heptene | 2.4 | 1.22 | 0.90 | 1.30 |
| E | toluene | 10.0 | 8.73 | 11.74 | 8.78 |
| F | 1-octene | 3.1 | 2.83 | 1.17 | 2.97 |
| G | ethylbenzene | 10.9 | 12.5 | 6.96 | 12.4 |
| H | 1-nonene | 2.3 | 2.34 | 1.07 | 0.34 |
| I | styrene | 28.4 | 30.08 | 24.3 | 31.9 |
| J | allylbenzene | 4.4 | 4.92 | 2.86 | 5.26 |
| K | propylbenzene | 5.4 | 5.41 | 3.76 | 5.24 |
| L | 1-decene | 1.8 | 2.16 | 1.76 | 2.33 |
| M | 3-butenylbenzene | 2.5 | 3.16 | 2.66 | 3.02 |
| N | 1-undecene | 4.0 | 4.83 | 3.93 | 4.01 |
| O | 4-pentenylbenzene | 2.4 | 2.62 | 2.75 | 2.22 |

TABLE E5-2-continued

The products from the liquid fraction of the microwave promoted reaction of 1-phenyldodecane with a wood charcoal catalyst.[a]

| | Structure | | | | |
|---|---|---|---|---|---|
| P | Ph-CH2CH2CH2CH=CH2 | 2.4 | 2.29 | 3.18 | 2.39 |
| Q | Ph-(CH2)4CH=CH2 | 2.1 | 2.18 | 3.41 | 2.24 |
| R | Ph-(CH2)5CH=CH2 | 2.1 | 2.33 | 3.83 | 2.45 |
| S | biphenyl | 3.2 | 3.22 | 7.14 | 3.86 |
| T | Ph-(CH2)6CH=CH2 | 2.8 | 2.94 | 4.57 | 1.92 |
| U | Ph-(CH2)7CH3 | 1.9 | 1.88 | 4.25 | 1.79 |
| V | Ph-(CH2)7CH=CH2 | 1.0 | 1.27 | 2.91 | 1.31 |
| W | Ph-(CH2)8CH=CH2 | 2.3 | 1.71 | 3.79 | 1.19 |

| | Reaction 1 | Reaction 2 | Reaction 3 | Reaction 4 |
|---|---|---|---|---|
| Reaction Time (min) | 5 | 10 | 50 | 80 |
| Conversion (%)[c] | 8.9 | 14.1 | 18.1 | 27.7 |
| [gas/liquid][d] | 0.5 | 1.33 | 1.49 | — |

[a] A wood based charcoal (0.1 g, CENCO, Central Scientific Company, USA).
[b] Compounds A, B, C, D, E, F, G, H, I, J, K, L, N, S GC/IR and GC/MS compared with those of authentic compounds.
Compounds O, P, M, Q, R, T, U, V, W assigned the structures by GC/MS to those of Homologous compounds in the GC/MS and GC/IR libraries.

TABLE E5-3

The products from the liquid fraction of the microwave promoted reaction of 1-phenyldodecane with a char catalyst prepared from white pine.

| Products[a] | | Product Yield (%), Reactions 1–3 | | |
|---|---|---|---|---|
| A | CH3CH2CH=CH2 | 0.36 | 0.76 | 0.2 |
| B | CH3CH2CH2CH=CH2 | 0.7 | 1.72 | 0.48 |

TABLE E5-3-continued

The products from the liquid fraction of the microwave promoted
reaction of 1-phenyldodecane with a char catalyst prepared from white pine.

| | Structure | | | |
|---|---|---|---|---|
| C | benzene | 0.5 | 1.39 | 0.41 |
| D | 1-hexene | 0.6 | 1.48 | 0.73 |
| E | toluene | 3.3 | 7.00 | 5.75 |
| F | 1-heptene | 1.2 | 1.97 | 2.20 |
| G | ethylbenzene | 7.2 | 5.95 | 8.55 |
| H | 1-octene | 1.7 | 1.79 | 0.09 |
| I | styrene | 23.0 | 23.4 | 32.5 |
| J | allylbenzene | 4.7 | 4.46 | 5.39 |
| K | propylbenzene | 5.9 | 3.87 | 4.69 |
| L | 1-nonene | 2.6 | 2.42 | 2.45 |
| M | 3-butenylbenzene | 4.1 | 3.36 | 2.98 |
| N | 1-decene | 6.3 | 6.15 | 4.95 |
| O | 4-pentenylbenzene | 4.3 | 1.23 | 2.85 |
| P | 5-hexenylbenzene | 3.9 | 3.83 | 3.20 |

TABLE E5-3-continued

The products from the liquid fraction of the microwave promoted reaction of 1-phenyldodecane with a char catalyst prepared from white pine.

| | | | | |
|---|---|---|---|---|
| Q | [structure] | 3.7 | 7.04 | 6.04 |
| R | [structure] | 4.8 | 3.86 | 2.99 |
| S | [structure] | 6.6 | 6.86 | 4.99 |
| T | [structure] | 5.4 | 4.18 | 2.82 |
| U | [structure] | 3.8 | 3.82 | 2.89 |
| V | [structure] | 2.1 | 2.03 | 2.12 |
| W | [structure] | 1.9 | 1.41 | 0.85 |

| | Reaction 1 | Reaction 2 | Reaction 3 |
|---|---|---|---|
| Reaction Time (min) | 20[d] | 30[e] | 30[e] |
| Conversion (%)[b] | 16.3 | 25.1 | 22.0 |
| [gas/liquid][c] | — | — | 1.07 |

[a]Compounds A, B, C, D, E, F, G, H, I, J, K, L, N, S GC/IR and GC/MS compared with those of authentic compounds.
Compounds O, P, M, Q, R, T, U, V, W assigned the structures by GC/MS to those of Homologous compounds in the GC/MS and GC/IR libraries.
[b]Conversion (%) was calculated as the fraction of products in the liquid fraction.
[c]The ratio of the 1-phenyldodecane converted to the gaseous products (see Table 1) to that of liquid products.
[d]0.1 g of charcoal.
[e]0.05 g of charcoal.

Example 6

An amount (1 g) cyclododecane was mixed with the catalyst (0.05–0.1 g) and subjected to microwave radiation of 2450 MHz for 5–60 minutes. The gaseous products were collected and analyzed as in Example 5.

Because the as-received cyclododecane was a waxy solid, either the cyclododecane alone or the mixture of cyclododecane and catalyst was first heated (100° C.) to melt the cyclododecane before exposing it to microwave radiation. As received melted cyclododecane was used directly in reactions (reactions 1–2). When the cyclododecane was dissolved in hexane and dried over anhydrous MgSO$_4$, reactions 3–5, the reaction proceeded faster and the oxygenated materials were almost entirely excluded.

The reactions of cyclododecane with wood based carbon (CENCO, Central Scientific Company, USA) were repeated using cyclododecane which was dried in a solution in hexane (20 g in 100 mL of hexane) over anhydrous magnesium chloride for 1 hour. After drying the solution was filtered, solvent evaporated and cyclododecane was dried overnight over phosphorous pentoxide in a vacuum desiccator. (reactions 3–5).

The conversion to the gaseous products was quantitated by the weight loss of the reaction mixture during the reaction. The liquid/solid products of the reactions of cyclododecane were extracted with methylene chloride or hexane and analyzed by gas chromatography. The products were identified by their GC retention times, GC/IR and GC/MS and were compared to authentic materials where available.

The reactions of cyclododecane with wood based carbon (CENCO, Central Scientific Company, USA) were repeated using cyclododecane which was dried in a solution in hexane (20 g in 100 mL of hexane) over anhydrous magnesium chloride for 1 hour. After drying the solution was filtered, solvent evaporated and cyclododecane was dried overnight over phosphorous pentoxide in a vacuum desiccator. (reactions 3–5)

Product results are shown in Tables E6-1 to E6-3. Table E6-1 presents the gaseous products from cyclododecane. An important feature of these results is the production of ethylene and molecular hydrogen as the major gaseous products. The major products of the cyclic hydrocarbons arise from the loss of ethylene. Tables E6-2 and E6-3 show results for other cycloalkanes. Cyclododecane produces cyclodecane as the highest yield product, followed by ring opening products dodecane and dodecene. Cyclodecane and cyclooctane also follow the trend of predominate ring contraction (loss of ethylene) followed in importance by ring opening to form linear alkane and alkene. Cyclooctane also exhibits predominately ethylene loss and ring opening. Finally, as shown in Table E6-2, a further important result is the function of water and hydrocarbon conversion to ketones and alcohols. These results suggest that small amounts of water can function as an oxidant for alkanes.

TABLE E6-1

The Gaseous Products From the Microwave Promoted Reactions of Cyclododecane With a Carbon Catalyst[a]

| Reaction | Amount of Charcoal (g)[a] | Reaction Time (min) | Conversion % | Product Yield (%)[c] |||||| 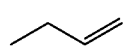 | 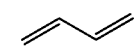 | 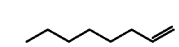 |
|---|---|---|---|---|---|---|---|---|---|---|---|
| | | | | $CH_4$ | $C_2H_4$ | $C_2H_6$ | $C_2H_2$ | $C_3H_6$ | | | |
| 1 | 0.1 | 60 | 3.0 | 5.54 | 73.8 | 1.08 | 4.35 | 7.74 | 2.83 | 2.27 | 2.42 |
| 2 | 0.1 | 120 | 7.4 | 4.58 | 68.9 | 0.96 | 6.31 | 8.95 | 4.41 | 5.26 | 0.62 |
| 3 | 0.1 | 300 | 15.0 | 3.50 | 66.9 | 1.32 | 3.65 | 7.21 | 7.71 | 7.74 | 1.92 |
| 4 | 0.05 | 120 | 3.7 | 3.33 | 71.7 | 1.89 | 0.88 | 10.2 | 6.43 | 4.46 | 1.11 |
| 5 | 0.05 | 240 | 5.7 | 3.28 | 73.9 | 2.91 | | 9.89 | 6.13 | 1.37 | 2.54 |
| 6 | 0.1 | 20 | 3.5 | 4.26 | 72.5 | 1.83 | 3.83 | 11.7 | 3.71 | 2.13 | — |
| 7 | 0.1 | 40 | 7.4 | 4.50 | 57.6 | 1.20 | 3.85 | 12.6 | 6.38 | 13.6 | 0.17 |

[a]Reactions 1–5 were carried out using a wood based charcoal and reactions 6–7 were carried out using white pine char.

TABLE E6-2

The Products of the Microwave Promoted Reaction of Cyclododecane with a Carbon Catalyst.[a]

| Products[b] | | Reaction 1[c] | Reaction 2[c] | Reaction 3[c] | Reaction 4[c] | Reaction 5[d] | Reaction 6[d] |
|---|---|---|---|---|---|---|---|
| | | | | Product Yield (%) | | | |
| A | (diene) | Tr | Tr | Tr | Tr | 0.477 | tr |
| B | (alkene) | 0.35 | 0.30 | Tr | Tr | 1.48 | tr |
| C | (cyclohexane) | 3.35 | 2.15 | 1.93 | 0.62 | 0.71 | 0.78 |
| D | (diene) | Tr | Tr | 0.56 | 0.48 | 0.34 | 0.62 |
| E | (alkene) | 0.29 | 0.27 | 1.25 | 1.14 | 1.14 | 1.53 |
| F | (diene) | 0.24 | 0.18 | 1.13 | 0.97 | 1.09 | 1.64 |
| G | (alkene) | 0.69 | 0.67 | 2.70 | 3.34 | 1.24 | 3.16 |
| H | (diene) | 0.57 | 0.43 | 1.59 | 1.89 | 3.37 | 3.07 |
| I | (alkene) | 0.22 | 0.32 | 2.05 | 1.69 | 2.87 | 2.43 |
| J | (cyclooctane) | 5.71 | 4.57 | 9.88 | 12.7 | 4.78 | 9.39 |
| K | (diene) | 2.98 | 2.29 | 8.47 | 8.52 | 1.65 | 10.38 |
| L | (alkene) | 0.80 | 1.53 | 0.62 | 0.85 | 7.00 | 0.88 |
| M | (propylcyclohexane) | 2.55 | 2.67 | 4.22 | 4.93 | 3.94 | 4.42 |
| N | (ethylmethylcyclohexane) | 3.27 | 10.64 | 1.86 | 1.65 | 2.71 | 4.01 |
| O | (methylcyclooctane) | 19.8 | 13.9 | 26.9 | 26.0 | 27.0 | 21.8 |
| P | (alkene) | 12.2 | 4.91 | 15.8 | 13.7 | 29.3 | 18.2 |

TABLE E6-2-continued

The Products of the Microwave Promoted Reaction of Cyclododecane with a Carbon Catalyst.[a]

| Q (cyclooctyl-propyl structure) | | 1.29 | 4.03 | 5.93 | 4.00 | 10.9 | 5.34 |
|---|---|---|---|---|---|---|---|
| R | Cyclododecanone | 26.4 | 30.6 | 8.35 | 9.93 | tr | 8.95 |
| S | Cyclododecanol | 19.3 | 20.6 | 6.67 | 7.46 | tr | 3.42 |

| | Reaction 1 | Reaction 2 | Reaction 3 | Reaction 4 | Reaction 5 | Reaction 6 |
|---|---|---|---|---|---|---|
| Reaction time (min) | 300 | 500 | 80 | 150 | 40 | 200 |
| Conversion (%)[e] | 3.9 | 6.3 | 2.4 | 3.8 | 8.6 | 15.7 |
| [gas/liquid][f] | 3.8 | — | 2.8 | 2.2 | 0.86 | 1.4 |

[a]Reactions 4–6 were carried out using cyclododecane dried over anhydrous magnesium sulfate.
[b]The products A, H, K, and N were identified by their gc/ms and gc/ir spectra and structures were assigned by analogy to the known spectra of their homologues. B, C, D, E, F, G, I, J, L, M, O, P, Q, R, and S were identified and their structures were assigned by comparing their gc/ir and gc/ms with those of authentic samples. The structure of P was also assigned by a comparison of its gc/ms with the library spectrum in the NIST collection. Small amounts (<0.5%) of decanal, dodecanal, methyl propyl cyclohexane, n-pentylcyclopentane, and methyl pentylcyclohexane were also detected.
[c]A wood based-charcoal (0.1 g, CENCO, Central Scientific Company, USA).
[d]A wood based charcoal prepared from white Pine.
[e]Conversion (%) was calculated as the fraction of products in the liquid fraction.
[f]The ratio of the cyclododecane converted to the gaseous products (see Table 2) to that of liquid products.

TABLE E6-3

Products of the Microwave Assisted Reaction of Cyclododecane with a Carbon Catalyst[a]

| Products[b] | | Product Yield (%)[c] | | | |
|---|---|---|---|---|---|
| | | 20 min | 60 min | 75 min | 175 min |
| (structure) | A' | — | — | 0.3 | — |
| (structure) | B' | — | — | 1.5 | — |
| (structure) | A | — | — | 1.05 | — |
| (structure) | B | — | — | 3.42 | — |
| (structure) | C | 2.17 | 2.25 | 2.34 | 2.91 |
| (structure) | D | 1.59 | 2.01 | 1.33 | 1.65 |
| (structure) | E | 2.97 | 3.52 | 2.67 | 2.83 |
| (structure) | F | 1.97 | 3.30 | 3.12 | 2.63 |
| (structure) | G | 7.48 | 9.17 | 8.00 | 7.11 |
| (structure) | H | 5.86 | 9.07 | — | 10.1 |
| (structure) | I | 3.55 | 3.64 | — | 4.08 |

TABLE E6-3-continued

Products of the Microwave Assisted Reaction of Cyclododecane with a Carbon Catalyst[a]

| Products[b] | | | Product Yield (%)[c] | | | |
|---|---|---|---|---|---|---|
| | | | 20 min | 60 min | 75 min | 175 min |
|  | J | | 19.5 | 18.0 | 23.7 | 18.4 |
| 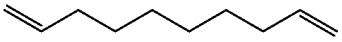 | K | | 1.34 | 3.05 | 2.7 | 3.03 |
| 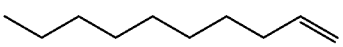 | L | | 10.3 | 10.3 | 10.5 | 10.3 |
| 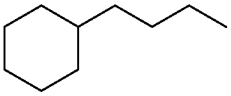 | M | | 4.4 | 4.32 | 3.96 | 4.77 |
| 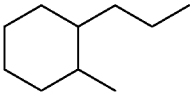 | N | | 1.69 | 1.83 | 1.55 | 2.99 |
| 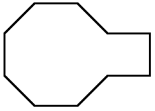 | O | | 21.3 | 16.8 | 16.8 | 15.5 |
| 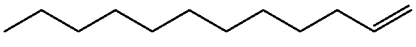 | P | | 14.0 | 12.7 | 17.1 | 13.7 |
| Gas (%)[d] | | | 13.2 | 13.0 | 14.8 | 28.7 |
| Liquid (%) | | | 5.3 | 7.4 | 6.4 | 16.5 |
| [Gas/Liquid] | | | 2.5 | 1.8 | 2.3 | 1.7 |
| Ring Contraction Products | | | 14.1 | 15.7 | 14.6 | 16.3 |
| Terminal Olefins | | | 55.6 | 55.2 | 57.9 | 51.0 |
| Diterminal Olefins | | | 16.1 | 11.8 | 12.1 | 18.0 |
| [H₂/Olefin][e] | | | 20.8 | 17.2 | 17.9 | 20.3 |
| [H₂/Diolefin][f] | | | 71.7 | 80.3 | 86.0 | 57.5 |

[a]A catalyst (0.2 g) made from white pine was used with 1 g of substrate.
[b]The solid/liquid products were dissolved in hexane and analyzed by gc (175 min) products were dissolved in nonane. The products A', A, H, K, and N were identified by their gc/ms and gc/ir spectra and structures were assigned by analogy to the known spectra of their homologues. B', B, C, D, E, F, G, I, J, L, M , O, P, Q, R, and S were identified and their structures were assigned by comparing their gc/ir and gc/ms with those of authentic samples. Thestructure of P was also assigned by a comparison of its gc/ms with the library spectrum in the NIST collection.
[c]The identified products accounted for more than 95% of the reaction mixture.
[d]The gaseous products were quantitated by the weight loss during the reaction.
[e]the mole ratio of total dihydrogen to liquid phase mono-olefin × 100.
[f]the mole ratio of total dihydrogen to liquid phase di-olefin × 100.

Example 7

An experiment was conducted to demonstrate bond cleavage of cyclodecane with microwave energy in the presence of a carbon or char catalyst. Experimental conditions and analyses were as for Example 6.

Results are shown in Tables E7-1. The results show that the major product is ring contraction by loss of ethylene to form cyclooctane. The next most important products are the $C_{12}$ ring-opened products. These products do not involve the loss of hydrogen, and therefore amount to disproportionation of the hydrocarbon rather than oxidation. This is illustrated by product L, which formed from breaking the C—C bond in cyclodecane and transfer of hydrogen from within the molecule to form an alkane end and an olefin end. Ring contraction was observed to form cyclooctane. The process of $C_8$ ring formation was shown to compete with hydrogen disproportionation to form mainly terminal olefin, product G. Similarly, $C_6$ ring formation appeared to compete with hydrogen disproportionation to form primarily B. An oxidative pathway that resulted in loss of two hydrogen atoms and formation of two olefins was shown to occur. The oxidative pathway is analogous to that observed for the acyclic substrate hexadecane, but leading to both olefinic sites in the same molecule, forming products A, D, and K.

TABLE E7-1

Products of the Microwave Assisted Reaction of Cyclodecane with a Carbon Catalyst[a]

| Products[b] | | Product Yield (%)[c] | |
|---|---|---|---|
| | | 10 min | 20 min |
| (structure) | A' | — | 0.73 |
| (structure) | B' | — | 1.72 |
| (structure) | A | 2.8 | 1.43 |
| (structure) | B | 3.96 | 2.41 |
| (cyclohexane) | C | 4.62 | 3.53 |
| (structure) | D | 3.58 | 2.41 |
| (structure) | E | 4.68 | 3.40 |
| (structure) | F | 2.65 | 2.94 |
| (structure) | G | 18.9 | 15.3 |
| (cyclooctane) | J | 32.3 | 32.4 |
| (structure) | K | Tr | 0.94 |
| (structure) | L | 18.7 | 21.5 |
| (structure) | M | 5.99 | 9.25 |
| (structure) | N | 1.93 | 2.05 |
| Gas (%) | | 10.8 | 24.2 |
| Liquid (%) | | 10.1 | 15.9 |
| [Gas/Liquid] | | 1.1 | 1.5 |
| Ring contraction | | 21.7 | 18.3 |
| Terminal Olefins | | 55.6 | 56.5 |
| Diterminal Olefins | | 14.0 | 15.1 |
| [H$_2$/Olefins] | | 11.1 | 12.8 |
| [H$_2$/Diolefin] | | 12.8 | 48.0 |

[a]A catalyst made from White Pine boiling splints (0.2 g) was used with 0.6 g of the substrate.
[b]The products were extracted with acetone (10 min reaction) or nonane (20 min reaction) and analyzed by gc. The products A', A, H, K, and N were identified by their gc/ms and gc/ir spectra and structures were assigned by analogy to the known spectra of their homologues. All other products were identified by comparison with authentic materials.
[c]The identified products accounted for more than 95% of the reaction mixture.

Example 8

An experiment was conducted to demonstrate oxidative and non-oxidative bond cleavage of cyclooctane using microwave energy and a carbon or char catalyst. The catalyst was prepared by heating white pine splints to 700–800° C. under a nitrogen atmosphere for 10 minutes.

The cyclooctane (1 g) was mixed with the catalyst (0.2 g) and subjected to the microwave radiation (2450 MHz for 0.75–1.7 hr). The products were collected and analyzed as in Example 6. The liquid/solid products of the reaction mixture were extracted with acetone, hexane or nonane and analyzed by gc, gc/ir and gc/ms and were compared to authentic materials where available.

Results are shown in Tables E8-1. The results show that the two major non-oxidative pathways, (1) $C_8$ ring cleavage and $C_2$ loss to form cyclohexane, E, competes with (2) hydrogen disproportionation to form I. In the non-oxidative pathway, the ratio of hydrogen atoms to carbon atoms remains unchanged on going from substrate to product.

TABLE E8-1

The Product distribution of the Microwave Assisted Reaction of Cyclooctane with a Carbon Catalyst[a]

| Products[b] | | Product Yield (%)[c] | | |
|---|---|---|---|---|
| | | 45 min | 65 min | 100 min |
| (structure) | A | — | — | 2.21 |
| (structure) | B | — | — | 7.96 |
| (structure) | C | 5.06 | 4.79 | 2.67 |
| (structure) | D | 5.99 | 5.65 | 3.65 |
| (cyclohexane) | E | 34.7 | 24.6 | 15.1 |
| (structure) | H | 3.47 | 5.18 | 4.59 |

TABLE E8-1-continued

The Product distribution of the Microwave Assisted Reaction of Cyclooctane with a Carbon Catalyst[a]

| Products[b] | | Product Yield (%)[c] | | |
|---|---|---|---|---|
| | | 45 min | 65 min | 100 min |
|  | I | 45.8 | 50.6 | 54.2 |
| 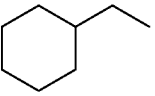 | S | 4.88 | 9.14 | 9.53 |
| Gas (%) | | 10.7 | 16.2 | 17.6 |
| Liquid (%) | | 3.5 | 4.8 | 3.5 |
| [Gas/Liquid] | | 3.1 | 3.4 | 5.0 |
| Ring Contraction Products | | 9.77 | 7.71 | 4.1 |
| Terminal Olefins | | 63.7 | 51.4 | 55.2 |
| Diterminal Olefins | | 11.0 | 24.4 | 19.2 |
| [H$_2$/Olefins] | | 18.9 | 24.3 | 29.3 |
| [H$_2$/Diolefin] | | 108.7 | 51.2 | 84.3 |

[a]0.2 g of the catalyst made from White Pine boiling splints were used with 1 g of the substrate.
[b]The products were dissolved in acetone and analyzed by gc. See footnote b, Table E6-3 for compound identification note. (The neat liquid was analyzed for 100 min reaction).
[c]The identified products accounted for more than 95% of the reaction mixture.

Example 9

A compilation of Examples 6, 7 and 8 for oxidative bond cleavage of cyclic hydrocarbons Is provided in Table E9-1. These results show that non-oxidative ring opening to form mono-olefins or ethylene loss and ring contraction predominate. Accordingly, hydrogen is formed in lower yields than olefins and ethylene.

Example 10

An experiment was conducted to demonstrate oxidative bond cleavage of Gas Oil (IBP 343 from Athabasca Bitumen (gas oil) with a carbon or char catalyst and with microwave exposure.

The reaction was carried out as in the examples for 1-phenyidodecane or cyclododecane using 1 g of the gas oil and 0.3 g of the catalyst prepared from white pine splints. The gaseous products were collected in a gas burette and analyzed by gas chromatography.

Results are shown in Table E10-1. Table E10-1 shows that a structurally diverse hydrocarbon source can provide ethylene as the major product in the present method of microwave catalyzed bond cleavage.

TABLE E9-1

The Distribution of the gaseous products of the microwave assisted reaction of cyclic Hydrocarbons with a carbon catalyst[a]

| Reaction time (min) | Conversion[b] (%) | Product Yield (%) | | | | | | | | |
|---|---|---|---|---|---|---|---|---|---|---|
| | | H$_2$ (T) | CH$_4$ (U) | C$_2$H$_4$ (V) | C$_2$H$_6$ (W) | C$_2$H$_2$ (X) | C$_3$H$_6$ (Y) |  (Z) | 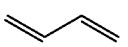 (i) | Others |
| Cyclodedecane | | | | | | | | | | |
| 25 | 12.9 | 16.2 | 3.85 | 46.7 | 1.82 | 11.6 | 8.38 | 3.33 | 6.70 | 2.48 |
| 45 | 17.4 | 14.9 | 2.23 | 50.7 | 1.21 | 9.28 | 9.40 | 4.26 | 4.43 | 3.63 |
| Cyclodecane | | | | | | | | | | |
| 20 | 24.2 | 12.0 | 2.63 | 48.6 | 0.40 | 4.20 | 8.96 | 6.99 | 14.5 | 1.77 |
| Cyclooctane | | | | | | | | | | |
| 45 | 10.7 | 16.0 | 4.00 | 58.8 | 0.41 | 3.67 | 4.43 | 4.43 | 8.16 | tr |
| 65 | 16.2 | 16.2 | 3.20 | 38.7 | 1.76 | 13.2 | 7.90 | 3.86 | 15.5 | 0.30 |
| 100 | 17.6 | 19.4 | 3.69 | 43.1 | 1.56 | 14.7 | 7.81 | 2.49 | 6.43 | 0.70 |
| Cyclohexane | | | | | | | | | | |
| 30 | 4.1 | 19.6 | 3.62 | 35.3 | 0.60 | 11.3 | 6.05 | 1.67 | 17.8 | 3.96 |
| 60 | 4.1 | 28.6 | 2.85 | 28.3 | 0.20 | 15.2 | 3.46 | 1.61 | 16.5 | 3.27 |

[a]A catalyst made from White Pine boiling splints (0.29 g) was used with 1 g of the substrate. 0.3 g of the catalyst was used for the 30 min. reaction of cyclohexane.
[b]Conversion to the gaseous products.

TABLE E10-1

The Gaseous Products From the Microwave Promoted Reactions of Gas Oil (IBP 343 from Bitumen) with a Carbon Catalyst.

| Amount of Charcoal (g) | Reaction Time (min) | Conversion (wt %) | Product Yield (%) | | | | | | | | |
|---|---|---|---|---|---|---|---|---|---|---|---|
| | | | $CH_4$ | $C_2H_4$ | $C_2H_6$ | $C_2H_2$ | $C_3H_6$ | 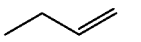 | 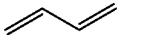 | 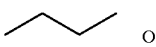 | Others |
| 0.1 | 60 | 2.0 | 9.13 | 46.5 | 0.57 | 8.67 | 12.9 | 3.83 | 14.3 | 0.23 | 3.85 |
| 0.2 | 60 | 9.4 | 12.0 | 32.3 | 6.86 | 0.96 | 27.2 | 10.0 | 6.24 | 1.24 | 4.10 |

Example 11

An experiment was conducted demonstrating use of a cyclic ketone.
Cyclododecanone 0.75 g of the substrate and 0.15 g of charcoal was irradiated as in Example 8 for 45 minutes, leading to gases (21.5%) and liquids (13.7%). The products included cyclodecanone, cyclooctanone, and cyclohexanone from single or multiple $C_2H_4$ loss, as well as 1-decene, 1-nonene, 1-octene, 1-heptene, 5-hexen-2-one, 1,8-nonadiene, and 1,7-octadiene. The products reflect CO loss, ketene ($CH_2CO$) loss, and $C_2H_4$ loss events.

Example 12

An experiment was conducted for cleaving an alkylaromatic compound according to the present invention. Conditions were as in Example 11.
Bibenzyl A sample of 0.2 g charcoal with 2 g of substrate produced 8% conversion to liquid products in 20 min. The products were benzene (1.3%), toluene (4.3%), ethylbenzene (0.2%), styrene (2.2%).

Example 13

An experiment was conducted to demonstrate reactions of several polycyclic hydrocarbons. The cleavage of bonds involving interconnected ring systems is illustrated. 1,2,3,4-Tetrahydronaphthalene—A 40-minute reaction of 1 g of substrate and 0.05 g of charcoal exhibited 10% conversion. The products were benzene, toluene, ethylbenzene, phenylacetylene, styrene, 2-methyl-1-ethylbenzene, 2-methylstyrene, indene, and small yields of dimers (5 isomers of molecular weight 260 and 262).

9,10-Dihydrophenanthrene—0.5 g of substrate and 0.1 g of charcoal was irradiated for 50 minutes to give 3.7% liquid products and 3% gases. The products included naphthalene, methylnaphthalenes, biphenyl, ethyinaphthalene, 2-methylbiphenyl, vinylnaphthalene, dimethyinaphthalene, stilbene, fluorene, methylfluorene, and 2-ethylbiphenyl.

Perhydrophenanthrene.—0.63 g of substrate and 0.1 g charcoal was irradiated for 25 minutes. The reaction gave gases (20.6%) and liquids (11.3%). The products included benzene, toluene, ethylbenzene, styrene, 2-propenylbenzene, cyclohexene, and vinylcyclohexene.

Example 14

Figure 2A:
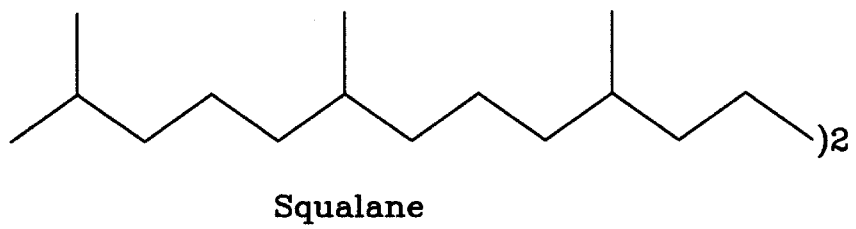
FIG. 2a is a chemical structure of squalane.
Figure 2B:
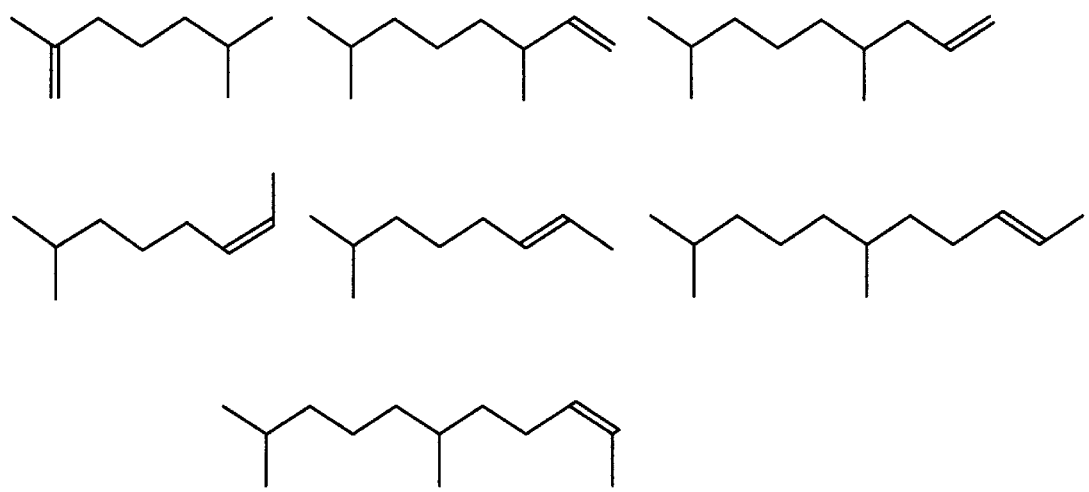
FIG. 2b shows chemical structures of products made from squalane.

An experiment was conducted to demonstrate the products formed from a branched alkane.
Squalane A sample of 0.1 g charcoal and 2 g squalane (FIG. 2a) was irradiated for 1 hour. A 61% yield of liquid products was observed. The liquid products contained a series of olefins from $C_5$ to $C_{27}$ in size chain. The product distribution was consistent with a fragmentation of squalane to give terminal and secondary olefins. When the fragmentation of the carbon backbone occurs at a branched position, both terminal and secondary olefins were formed. The products shown in FIG. 2b were formed which illustrate the cleavage pathways for the branched hydrocarbon. The gaseous products contained methane (10.5%), ethylene (35.8%), acetylene (2.1%), ethane (0.81%), propylene (31%), 1-butene and 2-methylpropene (8.8%) and others (6.8%). Hydrogen was not quantitated.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of microwave bond cleavage of a first hydrocarbon compound, the first hydrocarbon compound in a liquid phase and substantially non-aqueous, to a second compound having a shorter carbon chain than said first hydrocarbon compound, the method comprising the steps of:

(a) exposing a combination of the first hydrocarbon compound with a supported catalyst having a support of a non-metallic amorphous solid with at least one catalytic metal dispersed therein to microwave energy thereby oxidizing the first hydrocarbon compound into the second hydrocarbon compound, and molecular hydrogen; and (b) recovering the second hydrocarbon compound.

2. The method as recited in claim 1, wherein said supported catalyst has a ratio of said at least one catalytic metal to said support including the at least one catalytic metal less than 0.5 mg/10 mg support.

3. The method as recited in claim 1, wherein said non-metallic amorphous solid is carbon.

4. The method as recited in claim 1, wherein said supported catalyst is a char.

5. The method as recited in claim 4, wherein said char is selected from the group consisting of wood char, charcoal, and combinations thereof.

6. The method as recited in claim 5, wherein said charcoal is selected from the group consisting of wood charcoal, petroleum charcoal and combinations thereof.

7. The method as recited in claim 1, wherein said first hydrocarbon compound is selected from the group consisting of linear hydrocarbon with a carbon chain having at least 5 carbon atoms, branched hydrocarbon, cyclic hydrocarbon, and combinations thereof.

8. The method as recited in claim 7, wherein said second hydrocarbon compound is selected from the group consisting of α-olefin, hydrocarbon with olefin site, isomer, ring contracted cyclic hydrocarbon, and combinations thereof.

9. The method as recited in claim 7, wherein said first hydrocarbon compound is a derivatized hydrocarbon compound comprising the hydrocarbon compound and a derivative group.

10. The method as recited in claim 9, wherein said derivative group is selected from the group consisting of carboxylic acid, nitrile, alcohol, ester, ketone, and combinations thereof.

11. The method as recited in claim 10, wherein said derivative group is substantially unaltered during said oxidative or non-oxidative bond cleavage.

12. The method as recited in claim 9, wherein said derivatized hydrocarbon compound is dimethyladipate and said second hydrocarbon compound is methyl acrylate.

13. The method as recited in claim 9, wherein said derivatized hydrocarbon compound is an aliphatic carboxylic acid and said second hydrocarbon compound is a hydrocarbon of variable carbon chain number with a terminal olefin functional group and a terminal carboxylic acid functional group.

14. The method as recited in claim 7, wherein said second hydrocarbon compound is selected from the group consisting of an acyclic hydrocarbon, a cyclic hydrocarbon, and combinations thereof, and the hydrocarbon is exposed to water during the reaction resulting in the conversion of an alkane to an alcohol or a ketone.

15. The method as recited in claim 1, wherein said non-metallic amorphous solid is selected from the group consisting of carbon, alumina, manganese dioxide, magnetite, nickel oxide, iron oxide, calcium aluminate, cobalt oxide, chromium nitride, iron sulfide, copper sulfide and combinations thereof.

16. A method of microwave bond cleavage of a first hydrocarbon compound, the first hydrocarbon compound in a liquid phase and substantially non-aqueous, to a second compound having a shorter carbon chain than said first hydrocarbon compound, the method comprising the steps of:

(a) exposing a combination of the first hydrocarbon compound with a supported catalyst having a support of a carbon solid with at least one catalytic metal dispersed therein to microwave energy thereby converting the first hydrocarbon compound into the second hydrocarbon compound, and molecular hydrogen; and (b) recovering the second hydrocarbon compound.

17. The method as recited in claim 16, wherein said first hydrocarbon compound is selected from the group consisting of linear hydrocarbon with a carbon chain having at least 5 carbon atoms, branched hydrocarbon, cyclic hydrocarbon, and combinations thereof.

18. The method as recited in claim 17, wherein said second hydrocarbon compound is selected from the group consisting of $\alpha$-olefin, hydrocarbon with olefin site, isomer, ring contracted cyclic hydrocarbon, and combinations thereof.

19. The method as recited in claim 17, wherein said first hydrocarbon compound is a derivatized hydrocarbon compound comprising the hydrocarbon compound and a derivative group.

20. The method as recited in claim 19, wherein said derivative group is selected from the group consisting of carboxylic acid, nitrile, alcohol, ester, ketone, and combinations thereof.

21. The method as recited in claim 20, wherein said derivative group is substantially unaltered during said oxidative or non-oxidative bond cleavage.

22. The method as recited in claim 19, wherein said derivatized hydrocarbon compound is dimethyladipate and said second hydrocarbon compound is methyl acrylate.

23. The method as recited in claim 19, wherein said derivatized hydrocarbon compound is an aliphatic carboxylic acid and said second hydrocarbon compound is a hydrocarbon of variable carbon chain number with a terminal olefin functional group and a terminal carboxylic acid functional group.

24. The method as recited in claim 17, wherein said second hydrocarbon compound is selected from the group consisting of an acyclic hydrocarbon, a cyclic hydrocarbon, and combinations thereof, and the hydrocarbon is exposed to water during the reaction resulting in the conversion of the alkane to an alcohol or a ketone.

* * * * *